United States Patent [19]

Bastioli et al.

[11] Patent Number: 5,412,005

[45] Date of Patent: May 2, 1995

[54] BIODEGRADABLE POLYMERIC COMPOSITIONS BASED ON STARCH AND THERMOPLASTIC POLYMERS

[75] Inventors: Catia Bastioli; Vittorio Bellotti, both of Novara; Alessandro Montino, Pavia; Gianfranco D. Tredici, Varese; Roberto Lombi; Roberto Ponti, both of Novara, all of Italy

[73] Assignee: Novamont S.p.A., Milan, Italy

[21] Appl. No.: 876,474

[22] Filed: Apr. 30, 1992

Related U.S. Application Data

[63] Continuation-in-part of Ser. No. 875,453, Apr. 29, 1992, abandoned, Ser. No. 839,322, Feb. 20, 1992, abandoned, and Ser. No. 744,300, Aug. 13, 1991, Pat. No. 5,286,770.

[30] Foreign Application Priority Data

| | | | |
|---|---|---|---|
| May 3, 1991 | [IT] | Italy | TO91A0327 |
| Aug. 1, 1991 | [EP] | European Pat. Off. | 91112942 |
| Mar. 10, 1992 | [IT] | Italy | TO92A0199 |
| Mar. 27, 1992 | [IT] | Italy | TO92A0282 |

[51] Int. Cl.⁶ .......................... C08L 3/00; C08K 5/06
[52] U.S. Cl. ........................... 524/47; 524/48; 524/52; 524/53; 524/366; 524/377
[58] Field of Search ................... 523/126; 524/47, 48, 524/52, 53, 366, 377

[56] References Cited

U.S. PATENT DOCUMENTS

| | | | |
|---|---|---|---|
| 3,652,542 | 3/1972 | Hjermstad | 260/233.3 |
| 3,867,324 | 2/1975 | Clendinning et al. | 523/126 |
| 4,673,438 | 6/1987 | Wittwer et al. | 106/126 |
| 4,863,655 | 9/1989 | Lacourse et al. | 264/53 |
| 4,873,270 | 10/1989 | Aime et al. | 524/35 |
| 4,900,361 | 2/1990 | Sachetto et al. | 106/213 |
| 5,035,930 | 7/1991 | Lacourse et al. | 428/35.6 |
| 5,043,196 | 8/1991 | Lacourse et al. | 428/35.6 |
| 5,095,054 | 3/1992 | Lay et al. | 524/47 |

FOREIGN PATENT DOCUMENTS

| | | |
|---|---|---|
| 0032802 | 7/1981 | European Pat. Off. . |
| 0282451 | 9/1988 | European Pat. Off. . |
| 0298920 | 1/1989 | European Pat. Off. . |
| 0304401 | 2/1989 | European Pat. Off. . |
| 0326517 | 8/1989 | European Pat. Off. . |
| 0327505 | 8/1989 | European Pat. Off. . |
| 0409789 | 11/1989 | European Pat. Off. . |
| 0388924 | 9/1990 | European Pat. Off. . |
| 0391853 | 10/1990 | European Pat. Off. . |
| 0400532 | 12/1990 | European Pat. Off. . |
| 0404723 | 12/1990 | European Pat. Off. . |
| 0404727 | 12/1990 | European Pat. Off. . |
| 0404728 | 12/1990 | European Pat. Off. . |
| 0407350 | 1/1991 | European Pat. Off. . |
| 0408501 | 1/1991 | European Pat. Off. . |
| 0408502 | 1/1991 | European Pat. Off. . |
| 0408503 | 1/1991 | European Pat. Off. . |
| 0409781 | 1/1991 | European Pat. Off. . |
| 0409782 | 1/1991 | European Pat. Off. . |
| 0409783 | 1/1991 | European Pat. Off. . |
| 0409788 | 1/1991 | European Pat. Off. . |
| 248851 | 9/1992 | Japan . |
| 2190093 | 11/1987 | United Kingdom . |
| 8802313 | 3/1988 | United Kingdom . |
| WO90/10671 | 9/1990 | WIPO . |
| WO91/02023 | 2/1991 | WIPO . |
| WO91/02024 | 2/1991 | WIPO . |
| WO91/02025 | 2/1991 | WIPO . |
| WO93/00399 | 1/1993 | WIPO | C08L 3/02 |

OTHER PUBLICATIONS

Chemical Abstracts, vol. 7, No. 8, p. 47, Abstract No. 6015ln, F. H. Otey et al., "Starch-based blown films" (Aug. 24, 1987).

Otey, F. H. et al., Ind. Eng. Chem. Res. 26(8):1659–63 (1987), "Starch-Based Blown Films".

English Translation of Jap. Appl. No. 248851-1992.

Primary Examiner—Paul R. Michl
Assistant Examiner—LaVonda DeWitt
Attorney, Agent, or Firm—Bryan Cave

[57] ABSTRACT

The biodegradable polymeric compositions comprise a starch based component and a polymeric component comprising polymers of hydroxyacids or mixtures thereof with polymers deriving from ethylenically unsaturated monomers, particularly polymers of ethylene-vinylalcohol or polyvinylalcohol.

27 Claims, No Drawings

BIODEGRADABLE POLYMERIC COMPOSITIONS BASED ON STARCH AND THERMOPLASTIC POLYMERS

The present application is a continuation-in-part of U.S. Ser. No. 07/839,322 filed Feb. 20, 1992, now abandoned and a continuation-in-part of U.S. Ser. No. 07/875,453 filed Apr. 29, 1992, now abandoned, and a continuation-in-part of U.S. Ser. No. 07/744,300 filed Aug. 13, 1991, now U.S. Pat. No. 5,286,770.

present invention relates to polymeric compositions comprising starch and synthetic thermoplastic polymers, suitable for producing substantially biodegradable articles having satisfactory physical and mechanical properties by conventional techniques for the processing of thermoplastic materials.

Thermoplastic compositions of the type mentioned above are known and available on the market and are described for instance in patent applications Nos. EP-A-0 032 802, EP-A-O 327 505, WO 90/10671, EP-A-O 400 532, EP-A-0 404 723, EP-A-0 404 727, EP-A-O 404 728, WO 91/02024 and WO 91/02025.

Typically, these compositions are obtainable by blending a starch based component and a synthetic thermoplastic component under conditions which are typical of extrusion cooking, that is in the presence of a limited amount of water or plasticizer, (typically 5–40% by weight based on the starch-water system), at a temperature and pressure sufficient to destroy the crystallinity of starch and obtain a thermoplastic melt. By means of such process, thermoplastic blends have been obtained wherein the starch based component and the synthetic thermoplastic component form a structure which is interpenetrated or at least partially interpenetrated.

An object of the present invention is to provide novel polymeric compositions of the type mentioned above, which have a high biodegration rate and have improved mechanical properties and/or improved resistance to water and improved low permeability to water vapour in comparison with the corresponding properties of the known starch based compositions.

A further object of the invention is to improve processability of known biodegradable polymers, thereby to provide novel blends comprising such polymers, which are biodegradable and suitable to be more easily processed into finished articles, particularly sheets, films, and filaments.

The above objects are achieved by polymeric compositions of the type mentioned above, wherein the synthetic thermoplastic polymer component comprises one or more polymers selected from the group consisting of:
a) homopolymers of aliphatic hydroxyacids having from 2 to 24 carbon atoms, the corresponding lactones or lactides;
b) copolymers of a first monomer selected from the group consisting of aliphatic hydroxyacids having from 2 to 24 carbon atoms, the corresponding lactones or lactides with a second monomer selected from the group consisting of (1) aliphatic hydroxyacids having from 2 to 24 carbon atoms other than the first monomer, corresponding lactones or lactides, (2) aromatic and (3) hydroxyacids, aliphatic or aromatic isocyanates;
(c) block or graft copolymers between the homopolymers and copolymers (a) or (b) with one or more of the following components:

i) cellulose or modified cellulose such as cellulose acetate, or carboxymethylcellulose;
ii) amylose, amylopectin, natural or modified starches;
iii) polymers deriving from reaction of diols (such as ethylene glycol, propylene glycol, butylene glycol, polyoxyethylene glycol, polyoxypropylene glycol, neopentyl glycol, 1,4-butandiol, cyclohexandiol, or dianhydrous sorbitol), polyester prepolymers or polymers having diol terminal groups with:
  aromatic or aliphatic bifunctional isocyanates,
  aromatic or aliphatic bifunctional epoxydes,
  aliphatic bicarboxylic acids (such as malonic, succinic, maleic, fumaric, itaconic, glutaric, adipic, pimelic, suberic, azelaic, or sebacic acids),
  bicarboxylic cycloaliphatic acids (such as cyclohexan bicarboxylic acids, or 2,2,2-bicyclooctan bicarboxyllc acid),
  aromatic acids or anhydrides (such as phthalic acid),
iv) polyurethanes, polyamide-urethanes from diisocyanates and aminoalcohols, polyamides, polyester-amides from bicarboxylic acids and aminoalcohols, polyester-urea from aminoacids and diesters of glycols,
v) polyhydroxylated polymers (such as polyvinylalcohol), ethylene-vinylalcohol copolymers, totally or partially hydrolyzed, and polysaccharides up to dextrins,
vi) polyvinylpyrrolidone, polyvinylpyrrolidonevinylacetate copolymers, polyethyloxazolines;
vii) ionomeric polymers such as polyacrylates and polymetacrylates;
d) polyesters obtained from monomers or comonomers such as defined above at a) and b) upgraded with chain extenders such as isocyanates, epoxides, phenylesters and aliphatic carbonates;
e) polyesters obtained from monomers and comonomers defined at a) and b) above partially crosslinked by means of polyfunctional acids such as trimellitic acid, pyromellitic acid, polyisocyanates and polyepoxides.

Homopolymers and copolymers of epsilon hydroxyacids are preferred, particularly of 6-hydroxycaproic acid, 6-hydroxyoctanoic, 3,7-dimethyl-6-hydroxyoctanoic acid and corresponding lactones.

As monomers of aliphatic hydroxyacids having from 2 to 24 carbon atoms the following acids and corresponding lactides or lactones are particularly contemplated:
alpha-hydroxyacids such as lactic acids and the corresponding lactide, glycolic acid and the corresponding glycolide;
beta-hydroxyacids such as hydroxypropionic acid, hydroxypivalic and hydroxypelargonic acid and the corresponding lactone;
gamma-hydroxyacids such as hydroxybutyric and the corresponding lactone;
delta-hydroxyacids such as hydroxyvaleric acid and the corresponding lactone;
epsilon-hydroxyacids such as those mentioned above;
hydroxyacids having the hydroxy group placed beyond the 6-position such as 10-hydroxydecanoic acid; products of natural origin such as sabinic acid (12-hydroxydodecanoic) and juniperic acid (16-hydroxyhexadecanoic); unsaturated hydroxyacids such as ricinoleic acid; acids deriving from alpha-hydroxylation of fatty acids such as miristic, palmitic and stearic acids; acids deriving from hydroxylation of unsaturated fatty acids such as oleic, ricinoleic, linolenic and erucic acids;

cycloaliphatic hydroxyacids such as the hydroxyacids of cyclohexane and of 2,2,2-bicyclooctane.

As copolymers of aliphatic hydroxyacids with isocyanates, copolymers of epsilon-caprolactone with 4,4′-diphenylmethane-diisocyanate (MDI), tolylenediisocyanate (TDI), isophoron diisocyanate or hexanmethylen diisocyanate are preferred.

As the copolymers of aliphatic hydroxyacids and the corresponding lactones with aromatic hydroxyacids copolymers of epsilon-caprolactone with beta-phenyl lactic acid or mandelic acid are preferred.

The crystalline polymers a)–e) which are used in accordance with the present invention have typically a melting point of from 40° to 175° C.; however, both crystalline and amorphous polymers may be used; homopolymers and copolymers having a molecular weight above 40,000 are preferred.

It is known that aliphatic polyesters having low melting point or low glass transition temperature are difficult to process by conventional techniques for thermoplastic materials, such as film blowing and blow moulding. With reference particularly to poly-epsilon-caprolactone and its copolymers which have low melting points, films produced therefrom are tacky, as extruded, and noisy to the touch and have a low melt strength over 130° C.; moreover, due to the low crystallization rate of such polymers, the crystallization process proceeds for a long time after production of the finished articles with an undesirable change of properties with time. It has been found that the blending of starch with polymers a)–e) improves their processability properties without impairing the mechanical properties and biodegradability properties thereof; the improvement is particularly effective with polymers having low melting point temperatures of from 40° to 100° C.

The relative ratio between the starch component and the polymeric component may vary within wide limits depending upon the final use to which the blends of the invention are adapted. Typically ratios of from 1:9 and 9:1 are used, preferably of from 1:4 to 4:1, more preferably of from 1.5:1 to 1:1.5.

Preferred embodiments comprise blends wherein the polymeric component consists of poly-epsilon-caprolactone, preferably with a molecular weight above 40,000, or of a copolymer of epsilon-caprolactone and aliphatic or aromatic isocyanates, such as the copolymer Estane (registered trademark, BF Goodrich), or mixtures thereof having a weight ratio preferably of from 5:1 to 1:1.

According to another embodiment of the invention, the synthetic polymeric component comprises a component A consisting of polymers cited at items a) through e) or mixtures thereof and a component B comprising one or more polymers or copolymers derived from ethylenically unsaturated monomers having repeating units provided with at least one functional polar group, such as preferably hydroxyl or carboxyl, carboxyalkyl, alkylcarboxyl, pyrrolidyl and acetal, (alkyl is meant to include preferably C1–C4).

The polymers of component B comprise ethylene copolymers having melting point between 80° and 130° C. and an ethylene content higher than about 50% wt, such as particularly ethylene-acrylic acid, ethylene-vinylalcohol, and ethylene-vinylacetate copolymers and mixtures thereof. Particularly preferred are, however higher melting polymers, such as polyvinylalcohol and copolymers of ethylene-vinylalcohol with an ethylene content of from 10 to 44% by weight which are produced by hydrolysis of the corresponding polyvinylacetate and ethylene-vinylacetate, with hydrolysis degree between 50 and 100%.

Blends of starch and ethylene-vinylalcohol copolymers are described in U.S. patent application Ser. No. 530,925 filed May 29, 1990 (EP-A-0 400 532) the contents of which are hereby incorporated herein by reference.

The alcohol groups of the polymers mentioned above may be partially or completely modified to produce:

1) ethers resulting from reaction with:
   ethylene oxide
   ethylene oxide substituted with alkyl radicals up to $C_{20}$ or with aromatic radicals
   acrylonitrile ($Ce^{2+}$ initiator)
   acrylamide
   arylalkylhalides
   chloroacetic acid
   methylchloromethyl ether
   silanes 2) inorganic and organic esters such as sulphates, nitrates, phosphates, arsenates, xanthates, carbamates, urethanes, borates, titanates, 3) organic esters resulting from reaction with aliphatic or aromatic acids, chloroacyls, particularly of fatty acids or anhydrides, 4) acetals and ketals produced by reaction with
   aliphatic aldehydes with up to 22 carbon atoms,
   unsaturated aliphatic aldehydes with up to 22 carbon atoms,
   chloroacetaldehyde
   glyoxal
   aromatic aldehydes
   cyclic aliphatic aldehydes,
   aliphatic ketones
   arylalkyl ketones
   alkylcycloalkyl ketones.

The reactions which produce the ethers, organic and inorganic esters and the acetals given above can easily be brought about as described in Chapter 9 and in the literature cited in the publication "Polyvinyl alcohol" edited by C. A. Finch.

It is also possible to use multifunctional polymers of polyvinyl alcohol and of ethylene-vinyl alcohol (containing up to 40% by weight of ethylene with degrees of hydrolysis of the acetate of between 100 and 50%), in which up to 50% of the ethylene may be substituted by co-monomers selected from the group consisting of:

propylene, isobutene, styrene, vinyl chloride, 1,1-dichloroethene, vinyl ethers of the formula $CH_2=CR-OR'$ in which R is hydrogen or a methyl group and R′ is an alkyl group with from 1 to 18 carbon atoms, a cycloalkyl group or a polyether, acrylonitrile, methacrylonitrile, vinyl ketones of the formula $CH_2=CR-CO-CH_2-R'$ in which R is hydrogen or a methyl group and R′ is hydrogen or a $C_1-C_6$ alkyl group, acrylic or methacrylic acid and their esters of the formula $CH_2=CR-COOR'$ in which R is hydrogen or a methyl group and R′ is hydrogen or a $C_1-C_6$ alkyl group, and the alkali metal or alkaline-earth metal salts of those acids, vinyl derivatives of the formula $CH_2=CR-OCOR'$ in which R is hydrogen or a methyl group and R' is hydrogen, a methyl group, a methyl group mono-, bi-, or tri-substituted with chloro- or fluoro- groups, or a $C_2-C_6$ alkyl group, vinyl carbamates of the formula $CH_2=CR-CONR'R''$ in which R is hydrogen or a methyl group and R' and R'' are the same or different and are hydrogen or $C_1-C_3$ alkyl groups, maleic anhydride, fumaric anhydride, vinylpyrrolidone, vinylpyridine, or 1-vinylimidazole.

The copolymerisation is achieved with the use of free radical initiators such as hydrogen peroxide, peroxysulphates and benzoyl peroxides, as described in the chapter "Polymerisation processes of vinyl esters" and the literature cited on pages 406 et. seq. of Volume 17 of the "Encyclopedia of Polymer Science and Engineering"

Preferred compositions according to the invention comprise, as component A, poly-epsilon-caprolactone or its copolymers, preferably isocyanate copolymers, polyhydroxybutyrrate, polyhydroxybutyrrate/valerate, or lactic acid polymers or mixtures thereof and, as component B, poly-ethylene-vinyl alcohol, possibly modified as mentioned above, polyvinyl alcohol or poly-ethylene-acrylic acid or poly-ethylene-vinyl-acetate or mixture thereof.

According to a further embodiment, the invention comprises blends wherein the synthetic polymer component comprises, as component A, aliphatic polyesters, including the above mentioned polymers a) through e) and polymers obtained by polymerizations of aliphatic diols with bicarboxylic acids such as polyethylene and polybutylene adipate or sebacate and, as component B, the same polymers mentioned in the preceding paragraph.

Biodegradable polymeric compositions comprising starch and ethylene-vinyl alcohol copolymers are known and provide films having outstanding mechanical properties and fair properties of resistance to water. Such compositions suffer, however, from some drawbacks particularly relating to a loss of mechanical properties due to humidity changes; particularly at temperatures below 10° C. and at low humidity there is an undesirable increase of brittleness and loss of impact strength which constitutes a limitation in connection with their use in manufacturing articles for packaging and the like applications. On the other hand, as we have mentioned before, polymers a)-e), which generally have good biodegradability properties, are difficult to be processed and, due to their low melting point may be used only in a limited range of temperatures.

According to the invention, it has been found that the addition to polymers A of the starch component and of the B polymer component is suitable to improve the mechanical properties and achieve a lower permeability to water vapour and liquid water. Particularly, the addition of starch and polymers B component to polymers A has a nucleating effect, which, under the processing conditions of the blends of the invention, provides for a substantial increase of the rate of crystallization of polymers A. The advantage is particularly effective in connection with the production of films, sheets, fibers and filaments and molded articles by film blowing, extrusion, melt spinning, blow molding and injection molding.

Blends including starch, polymers B and plasticizers are available on the market under the trademark Mater Bi by Novamont and such blends may be used as a source for starch and B polymers to provide the blends of the present invention.

The weight ratio between component A and B of the synthetic polymeric component is preferably from 1:6 to 6:1, more preferably of f rom 1:4 to 4:1.

Preferred composition specifically adapted for injection molding comprise:
from about 20 to about 60% by wt starch component,
from about 10 to about 80% by wt, particularly from about 10 to about 50% by wt component A,
from 0 to about 45% by wt component B, particularly from about 2 to about 30% by wt component B, the percent amounts being expressed with reference to the sum of starch and total synthetic component.

With reference to compositions adapted for the production of films, sheets and the like, the preferred compositions comprise:
from about 5 to about 60% by wt starch component.
from about 40 to about 80% by wt component A,
from 0 to about 35% by wt, particularly from about 5 to about 30% by wt component B,
the percent amounts being expressed with reference to the sum of the starch and total synthetic component.

When the available product Mater Bi (Novamont trademark) is used as the source for starch and type B polymers, preferred weight ratios between type A polymer and Mater Bi are from 80:20 to 30:70.

The starch used in the polymeric compositions is preferably a native starch extracted from vegetables such as potatoes, rice, tapioca, maize and cereals. In any case, the term starch is intended also to include physically and chemically modified starches.

It has been found that the use of a starch component comprising at least 78% by wt amylopectin allows one to obtain films by extrusion blowing, the cross section of which, when observed by scanning electromicroscopy (X 2,000 magnification), shows a layered or lamellar structure made by a plurality of linear polymeric microphases alternated with starch micro phases in which the crystalline structure of starch is no longer identifiable. The achievement of such layered structure substantially increases the barrier properties against gases and liquids of films and sheets obtained from such polymeric blends.

In this respect a starch component having an amylopectin content higher than 90% by wt and more desirably higher than 94% by wt is preferred. A starch component complying with the above requirements may be obtained by using waxy starch (amylopectin content of about 95% by wt) as the sole starchy material, or mixtures of amylopectin, waxy starch and/or conventional starch with lower amylopectin content such as maise starch and potato starch.

On the other hand a starch component having an amylopectin content lower than about 78% by wt and correspondingly an amylose content higher than about 22% by wt appears to favour, under the processing conditions of extrusion and film blowing, an interpenetration of the starch component with the synthetic polymer component.

The above mentioned layered or lamellar structure may also be obtained by use of a starch component having a lower amylopectin content, higher than about 70% wt, by adding to the blend being extruded any substance which is capable of reducing the complexing power of amylose or capable of interacting with starch by means of hydrophilic interactions such as boric acid, borax, metaboric acid, aluminium hydroxide and alkali metals salts, particularly chlorides. For that purpose an effective amount of such substances is of from 0.01 to 10% by wt, preferably of from 0.05 to 5% by wt, based on the starch component.

The addition of boron containing compounds in order to improve transparency of starch/polymer blends is described in U.S. Ser. No. 734492 filed Jul. 23, 1991, the contents of which are hereby incorporated herein by reference.

The polymeric composition preferably includes a plasticizer at a concentration of from 1 to 50% by weight, preferably from 5 to 40%, more preferably from 5 to 25% by wt, with reference to the weight of the total composition consisting of the starch and polymeric component(s). Polyols selected from the following may be used as the plasticizer:

a) polyols formed by from 1 to 20 repeating hydroxylated units each including from 2 to 6 carbon atoms.

b) ethers, thioethers, inorganic and organic esters, acetals and amino-derivatives of polyols formed by from 1 to 20 repeating hydroxylated units each including from 2 to 6 carbon atoms, c) reaction products of polyols having from 1 to 20 repeating hydroxylated units each including from 2 to 6 carbon atoms with chain extenders, d) oxidation products of polyols having from 1 to 20 repeating hydroxylated units each including from 2 to 6 carbon atoms including at least one aldehydic or carboxylic functional group or a mixture thereof.

Compounds which have vapour pressures below that of glycerine at ambient temperature (25° C.) and which are soluble in water are preferred, in order to reduce bleeding or sweating phenomena of the plasticizer from finished articles obtained from the compositions of the invention.

The aliphatic polyols of type a) include compounds of the formula:

$$OH-CH_2-(CHOH)_n-OH_2OH \quad (I)$$

in which n is from 0 to 4, such as ethylene glycol, glycerol, erythritol, arabitol, adonitol, xylitol, mannitol, iditol, galactitol, sorbitol and allitol and polyols which do not fall within the formula given above, such as propylene glycol, polyglycols, trimethylolpropane, pentaerythritol, polyvinylalcohol with from 3 to 20 repeating units, and polyglycerol formed by from 2 to 10, preferably from 2 to 5, monomeric units, including mixtures of various oligomers.

The aliphatic polyol derivatives of paragraph b) preferably have structural formulae which can be obtained by the substitution of at least one alcoholic functional group of the polyol in question, which is preferably selected from those cited in the preceding paragraph, by a functional group selected from:

—O—(CH$_2$)hd n —H in which n=1-18, preferably 1-4,

—O—CH=CH—R$_1$ in which R$_1$=H or —CH$_3$,

—O(CH$_2$—CHR$_1$—O)$_n$—H in which R$_1$=H or CH$_3$ and n=1-20,

—O—(CH$_2$)$_n$—Ar in which Ar is a simple, substituted, or heterocyclic aromatic radical and n=0-4,

—OCO—H,

—OCO—CR$_1$R$_2$R$_3$ in which the R$_1$, R$_2$, and R$_3$ groups are the same or different and are selected from H, Cl, and F, —OCO—(CH$_2$)$_n$—H in which n=2-18, preferably 2-5,

—ONO$_2$,

—OPO$_3$M$_2$ in which M may be H, ammonium, an alkali metal, an alkaline earth, metal or an organic cation, particularly trimethylammonium, pyridinium or picoline, —SO$_3$—Ar in which Ar is benzene or toluene, —OCO—CH(SO$_3$M)—COOM in which the M's are the same or different and are selected from H, an alkali metal, an alkaline-earth metal, ammonium, and an organic cation, particularly pyridinium, picoline or methylammonium, —OCO—B—COOM in which B is (CH$_2$)$_n$, in which n=1-6 or —CH=CH—, M may be H, an alkali metal, an alkaline-earth metal, or —(CH$_2$)$_n$H, in which n=1-6, or an aryl group, —OCONH—R$_1$ in which R$_1$ may be —H or an aliphatic or aromatic radical, —O—(CH$_2$)$_n$—COOM in which n=1-6 and M may be H, an alkali metal, an alkaline-earth metal, ammonium, or an organic cation, particularly pyridinium, trimethylammonium, or picoline, —O—(CH$_2$)$_n$—COOR$_1$ in which n=1-6, R$_1$=H(CH$_2$)$_m$— in which m=1-6.

—NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1-4, R$_1$ and R$_2$=H, CH$_3$—, CH$_3$CH$_2$—, or CH$_2$—CH$_2$OH, and in which the amino group may be salified,

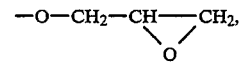

—O—CH$_2$—CHOH—CH$_2$—NR$_1$R$_2$ in which R$_1$ and R$_2$ are the same or different and are selected from H, and H(CH$_2$)$_n$ in which n=1-6 and in which the amino group may be salified, —O—(CH$_2$)—CHOH—CH$_2$—R$^+$$_1$Cl$^-$ in which R$^+$$_1$ is a trialkylammonium, pyridinium or picoline group, —O—(CH$_2$)$_n$R$^+$$_1$Cl$^-$ in which n=1.14 6 and R$^+$$_1$ is a trialkylammonium, pyridinium or picoline group, —O—(CH$_2$)$_n$—CN in which n=1-6, —O—(CH$_2$)$_n$—CONH$_2$ in which n=1-6, —O—(CH$_2$)$_m$—SO$_2$—(CH$_2$)$_n$—H in which m and n=1-4, —SCSNH$_2$, —O—SiX$_3$ and —O—SiOX$_3$ in which X may be an aliphatic or an aromatic radical.

Mono- and di-ethers and mono- and di-esters of the polyols of formula (I) given above are particularly preferred and monoethoxylate, monopropoxylate, and monoacetate derivatives, particularly of sorbitol, are most preferred.

The compounds of paragraph c) result from the joining of two or more polyol molecules by means of chain extenders, in particular such as bicarboxylic acids, aldehydes and isocyanates.

Preferred compounds are of the formula:

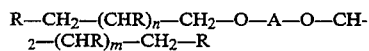

R—CH$_2$—(CHR)$_n$—CH$_2$—O—A—O—CH-$_2$—(CHR)$_m$—CH$_2$—R in which n and m are the same or different and have values of from 1 to 6, the R groups are the same or different and are hydroxyl groups or have the meaning given above, and in which A is selected from the group consisting of:

—CHR$_1$ in which R$_1$=H or H—(CH$_2$)$_n$—, in which n=1-5 (acetals),
—(CH$_2$)$_n$— in which n=1-6,
—(CH$_2$—O—CH$_2$)$_n$ in which n=1-20,
—(CH$_2$CH$_2$—O)$_n$—CH$_2$CH$_2$— in which n=1-20,
—OC—(CH$_2$)$_n$—CO— in which n=b 0-6,
—OC—Ar—CO— in which Ar is an aromatic radical which is also heterocyclic.
—PO$_2$—,
—CONH—(CH$_2$)$_n$NHCO—,
and compounds of the formula:

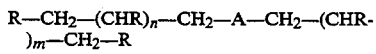

in which n and m are the same or different and are whole numbers from 1 to 6, the R groups are the same or different and are hydroxyl groups or have the meaning given above, and in which A is selected from the group consisting of NH— and —NH—(CH$_2$—CH$_2$—NH)$_n$— in which n is a whole number from 1 to 6.

Of the compounds given above, compounds in which only one of the R groups is a group forming an ether or an ester are preferred.

The term "polyol" is intended to include mono- and polysaccharides having up to 20 monosaccharide units.

The following monosaccharides are considered in particular:

pentoses and their derivatives of the formula:

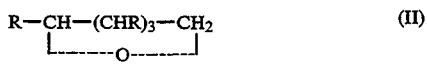

in which the R groups are the same or different and are hydroxyl groups or have the meaning given above.

Examples of these compounds are arabinose, lyxose, ribose and xylose and, preferably, their monoethers and monoesters, aldohexoses and their derivatives of the formula:

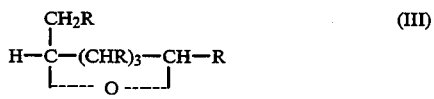

and ketohexoses and their derivatives of the formula:

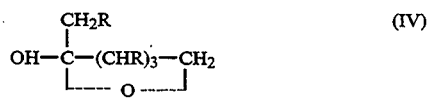

in which the R groups are the same or different and are hydroxyl groups or have the meaning given above.

Examples of these monosaccharides are glucose, fructose, mannose, allose, altrose, galactose, gulose, idose, inositol, sorbose and talitol.

Of their etherified or esterified derivatives, monoethoxylate and monopropoxylate derivatives and monoesters, particularly of acetic acid, are preferred.

The polysaccharides include compounds having up to 20 repeating units of formula (II), (III) or (IV) with molecular weights up to chat of dextrin.

The R functional groups may be introduced into the basic structure of the polyol by known reactions, for example, as described in Chapter 9 and in the literature cited in the publication "Polyvinyl alcohol" edited by C. A. Finch.

Preferred plasticizers comprise: glycerine, polyglycerol, glycerol ethoxylate, ethylene or propylene glycol, ethylene or propylene diglycol, ethylene or propylene triglycol, polyethylene or polypropylene glycol, 1,2-propandiol, 1,3-propandiol, 1,2-, 1,3-, 1,4-butandiol, 1,5-pentandiol, 1,6-, 1,5-hexandiol, 1,2,6-, 1,3,5-hexantriol, neopentylglycol, trimethylolpropane, pentaerythritol, sorbitol acetate, sorbitol diacetate, sorbitol monoethoxylate, sorbitol dipropoxylate, sorbitol diethoxylate, sorbitol hexaethoxylate, aminosorbitol, trihydroxymethylaminomethane, glucose/PEG, the product of reaction of ethylene oxide with glucose, trimethylolpropane monoethoxylate, mannitol monoacetate, mannitol monoethoxylate, butyl glucoside, glucose monoethoxylate, alpha-methyl glucoside, the sodium salt of carboxymethylsorbitol, polyglycerol monoethoxylate and mixtures thereof.

If synthetic polymers with high melting points such as, for example, polyvinyl alcohol and ethylene-vinyl alcohol copolymer with an ethylene content no greater than 44% by weight are used as component B, the described plasticizers may also perform an important function in the process which leads to the formation of a composition with an (at least partially) interpenetrated structure. The melting points of these polymers (160°-200° C.) are so high that complete interpenetration with the starch molecules is not possible; the addition of plasticizers common to the starchy and polymeric components lowers the melting points of the synthetic polymers and, at the same time, changes their theological behaviour.

The polymeric material may also include agents, such as urea or hydroxides of alkali metals or of alkaline-earth metals, which can destroy hydrogen bonds and of which quantities of between 0.5 and 20% by weight with reference to the weight of the entire composition are added to the mixture of starch and copolymer.

The addition of urea, in the preferred amount of from 5 to 20% by wt, is advantageous particularly for the production of blends for film-blowing.

The composition of the invention may also comprise relatively low amounts of hydrophobic polymers, such as polyethylene, polypropylene and polystyrene; however, in order not to impair the biodegradability properties, the amount of such polymers should preferably not exceed about 5% by wt of the overall composition, The polymeric composition of the invention may also include cross-linking agents such as aldehydes, ketones and glyoxals, process coadjuvants and release agents, and lubricants which are normally incorporated in compositions for moulding or extrusion, such as fatty acids, esters of fatty acids, higher alcohols, polythene waxes, LDPE, fungicides, flame-proofing agents, herbicides, antioxidant, fertilisers, opacifiers and stabilisers.

Further additives comprise polyvinylpyrrolidone, polyoxazoline, cellulose acetates and nitrates, regenerated cellulose, alkyl cellulose, carboxymethyl cellulose, casein-type proteins and salts thereof, natural gums such as gum arabic, algin and alginates, chitin and chitosan.

The polymeric compositions are preferably prepared by the mixing of the components cited above in an extruder heated to a maximum temperature generally between 100° and 220° C. by the methods described in patent applications EP-A-413798 and EP-A-400532 incorporated herein by reference. The composition supplied to the extruder includes water due to the intrinsic water content of the starch used (9–15% by weight) and water may be added as appropriate.

The composition of the invention have preferably a water content of from 1.5 to 5% wt, as extruded, before conditioning, which is obtained by reducing the initial water content of the total composition during the extrusion by intermediate de-gassing.

The pressures to which the mixture is subjected during the thermal processing treatment are typical for extrusion in single or double-screw extruders. Although the process is preferably carried out in an extruder, the starch, synthetic polymer and plasticizer may be mixed by any device which ensures conditions of temperature and shearing stress suitable to make the starch and the polymer used compatible from a theological point of view.

The method for preparing the compositions of the invention. under the preferred conditions, includes the following steps:

swelling the starch component and the synthetic polymer component by means of the plasticizer, and possibly water, at a temperature of between 80° and 180° C. with a dynamic change in their melting points and theological behaviour; this effect can be achieved, for example, during a first stage of the transportation of the components through an extruder, for periods of the order of from 2 to 50 seconds, subjecting the mixture to shearing conditions corresponding to similar viscosity values of the plasticized starch and synthetic polymer components, de-gassing freely or in a controlled manner under pressure or under vacuum to produce a melt at a temperature of 140°–180° C. with a liquid content such that bubbles are not created at atmospheric pressure, that is, for example, at the output of the extruder.

cooling the finished product in a water bath or in air.

The entire method requires a pressure of between 0.5 and 10 MPa, preferably between 1 and 5 MPa.

As stated, the thermoplastic composition is preferably prepared by mixing the components mentioned directly, but the starch may also be treated beforehand in the presence of plasticizers, and possibly added water, with temperature conditions of from 100° to 220° C. to produce a thermoplastic starch. This starch may be mixed with the synthetic polymer and a further quantity of plasticizer during a second step. For polyvinyl alcohol and ethylenevinyl alcohol copolymer, a portion of the total quantity of plasticizer is added at the start of the mixing of the pretreated starch and the synthetic polymer since the plasticizer has to be available to modify the melting point and theological behaviour of the polymer to make it compatible with the starch.

The blends of the invention, may be obtained by direct blending, preferably by means of a conventional extruder, of starch and polymeric components A and B, when the latter is used or, according to the latter embodiment, by blending the component A polymer a) to e) with previously obtained blends obtained from starch and B polymers.

EXAMPLE 1

38 parts of Maize starch Globe 03401 (Cerestar, registered trademark, intrinsic water content 12% wt), 38 parts of ethylene-vinylalcohol copolymer with an ethylene molar content of 44% and hydrolysis degree of the acetate groups of 99.5%, 5 parts urea, 0.3 parts Armide E, 12 parts sorbitol mono-ethoxylated, 3.7 parts glycerine and 3 parts water were fed to a twin screw extruder OMC of 58 mm, L/D equal to 36, provided with 9 heating zones with a degassing section. The following operative conditions were selected for the extrusion process:

Screw speed (rpm): 170
degassing pressure (bar): 0.9
position of the degassing section: 8th zone
thermal profile: cold zone/90° C./140° C./180° C./180° C./180° C./180° C./175° C./165° C.
head temperature: 145° C. with melt temperature: 145° C.
head pressure (bar): 27
absorption (A): 67–69

The extrudate in spaghetti-like form was cooled in a water bath and transformed into pellets; the pellets had an intrinsic water content of 3.5% by weight (product named in the following pellet A1).

The following composition:
70 parts of poly-epsilon-caprolactone (PCL "TONE P-787", registered trademark Union Carbide)
30 parts of the pellets A1
4 parts glycerine was fed to an OMC extruder, diameter 20 mm, compression ratio 1:3, having four controlled temperature zones, without intermediate degassing section, operating under the following conditions:

screw speed: 45 rpm
thermal profile: 140°/145°/150°/155° C.

The extrudate in spaghetti-like form was transformed into pellets (pellets A2). The pellets A2 were fed to a HAAKE extruder with a diameter of 19 mm and L/D equal to 25, operating at a speed of 45 rpm with the thermal profile: 140° C./145° C./150° C./155° C., provided with a blowing head, and transformed into films having a thickness between 30 and 50 micron. The mechanical properties of the obtained films are given in Table 1.

EXAMPLE 2

The procedure of example 1 was repeated by using in formulating the pellets A2 the following composition:
70 parts PCL "TONE P-787" (Union Carbide)
30 parts of the pellets A1
6 parts glycerine The mechanical and permeability properties are given in Table 1.

EXAMPLE 3

The procedure of example 1 was repeated by using in formulating the pellets A2 the following composition:
60 parts PCL "TONE P-787" (Union Carbide),
40 parts of the pellets A1

The mechanical properties are given in Table 1.

EXAMPLE 4

The procedure of example 1 was repeated by using in formulating the pellets A2 the following composition:
50 parts PCL "TONE P-787" (Union Carbide),
50 parts of the pellets A1

The mechanical and permeability properties are given in Table 1.

EXAMPLE 5

50 parts of the pellets A1 and 50 parts of poly-epsilon-caprolactone P-787 (Union Carbide) were fed to same OMC extruder used for the production of pellets A1 without intermediate degassing section operating under the following conditions:
  Screw speed: 130 rpm
  thermal profile: first cold zone/90° C./130° C./150° C./155° C./160° C./160° C./160° C./150° C.
  head temperature: 145° C.
  pressure: 32 bar
  absorption: 105 A
  productivity: 60 kg/h The thus obtained pellets were fed to a blowing apparatus with a diameter of 44 mm and L/D equal to 30, provided with a film blowing head having the following features:
  die diameter: 100 mm
  die gap: 0.5 mm
  die land: 10

The conditions for film blowing were the following:
  Screw speed: 65 rpm
  thermal profile of the extruder: 135° C./140° C./140° C./140° C.
  neck thermal profile: 140° C.
  head thermal profile: 135° C.
  draw ratio: 3.1
  blow-up ratio: 3.2

Films having an average thickness of 50 microns were obtained. The tensile properties and tear strength properties and permeability of the thus obtained films are given in Table 2.

EXAMPLE 6

The procedure of example 5 was repeated by feeding to the film blowing device a composition comprising 47.5% wt of the pellets A1, 50% wt of poly-epsilon-caprolactone and 2.5% wt polyethylene. The features of the thus obtained films are given in Table 2.

EXAMPLE 7

The procedure of example 5 was repeated by feeding to the film blowing device a composition comprising 47.5% wt of the pellets A1, 50% wt of poly-epsilon-caprolactone and 2.5% wt urea. The features of the films are given in Table 2.

EXAMPLE 8

The procedure of example 5 was repeated by feeding to the film blowing device pellets obtained from 48.5% wt of the pellets A1, 48.5% wt of poly-epsilon-caprolactone, 2.4% wt water and 0.6% wt glycerine. The features of the thus obtained films are given in Table 2.

EXAMPLES 9-16

The procedures of examples 1-8 were repeated by using, instead of poly-epsilon-caprolactone P-787 (Union Carbide) alone, a blend 4:1 wt of the latter and of a copolymer derived from epsilon-caprolactone and bifunctional isocyanate (polyester/urethane) produced by BF Goodrich (Estane, registered trademark); the properties of the thus obtained films were comparable to those of the films obtained according to examples 1-8.

EXAMPLES 17-23

To a twin screw extruder APV having a diameter of 30 mm and L/D equal to 25, the composition given in the following Table 3 were directly fed. In some cases, which are indicated by an asterix in Table 3, the poly-epsilon-caprolactone polymer was pre-blended with ethylenevinylalcohol copolymer (ethylene molar content 44%, hydrolysis degree 99.5%) by means of an extruder. The APV extruder was operated according to the following conditions:
  Screw speed: 170 rpm
  productivity: 13.1 kg/h
  thermal profile: first cold zone/60° C./160° C./165° C./170° C./170° C./170° C./170° C./160° C./150° C.
  head temperature: 140° C.

The extrudate in spaghetti-like form was pelletized and then fed to an injection moulding press Sandretto to produce dumb-bell specimen (ASTM 638) which were subjected to tests in order to determine their mechanical properties. The mechanical properties are given in Table 3.

EXAMPLE 24-25: BLOW-MOLDING

The following compositions were directly processed by blow-molding to produce plastic bottles:

|  |  | Ex 24 | Ex 25 |
| --- | --- | --- | --- |
| Starch (*) | % wt | 44.6 | 44.6 |
| PCL P-787 (**) | % wt | 41.4 | — |
| Estane (***) | % wt | — | 41.1 |
| Glycerine | % wt | 11.8 | 11.8 |
| Water (added) | % wt | 2.5 | 2.5 |

*Starch Globe 03401 (Cerestar, water content 12% wt)
**Union Carbide
***BF Goodrich The above compositions were fed to a AEMME blow-molding apparatus having a constant taper screw (compression ratio 1:3) with a diameter of 30 mm, L/D equal to 25 with the following operative conditions:
  mold type: round bottle, diameter 50 mm
  cooling system: water 17° C.
  air pressure: 6-7 bar

|  |  |  | Ex 24 | Ex 25 |
| --- | --- | --- | --- | --- |
| cylinder | T1 | °C. | 100 | 150 |
|  | T2 | °C. | 100 | 150 |
|  | T3 | °C. | 105 | 150 |
| head | T4 | °C. | 110 | 150 |
|  | T5 | °C. | 115 | 150 |
| screw speed: | rpm |  | 42 | 42 |
| parison speed | m/min |  | 0.7 | 0.7 |
| melt T (T3) | °C. |  | 106 | 147 |
| blowing time | sec |  | 11 | 10 |
| bottle weight | g |  | 22.9 | 21.8 |
| wall thickness | mm |  | 0.75 | 0.75 |

No relevant difficulties were found in the production of the bottles by blow-molding under the above described conditions. Comparative tests carried out under the same operative conditions with the use of poly-epsilon-caprolactone P-787 alone gave rise to difficulties such as the need to substantially increase the blowing time and problems of tackiness.

EXAMPLE 26-27

The procedure of Example 1 for the production of pellets A1 was repeated with the use of a waxy starch having an amylopectin content of about 95% wt and intrinsic water content equal to about 12% wt (Snowflake 04201 starch, registered trademark).

The thus obtained pellets were blended with poly-epsilon caprolactone P 787 (Union Carbide) directly in the film blowing apparatus Ghioldi under the following conditions with a weight ratio (pellets/poly-caprolactone) 50/50 (Ex 26) and 60/40 (Ex 27) by weight.
 Ghioldi apparatus: diameter 40mm and L/D 30
 screw: constant taper, compression ratio 1:2.8
 shape: spiral
 die diameter: 100 mm
 die gap: 0.5 mm
 die land: 10
 Film blowing conditions:
 screw speed: 65 rpm
 thermal profile of the extruder: 135°/135°/140°/140° C. (melt temperature: 152° C.)
 neck thermal profile: 140°–140° C. (melt temperature 152° C.)
 head thermal profile: 135°–135° C. (melt temperature 140° C.)
 neck pressure: 274 bar die pressure: 73 bar
 draw ratio: 3
 blow-up ratio: 3

The mechanical and permeability properties to water vapour (determined by the method of Lissy 39° C., R.H. 90%) and to liquid water (20° C., part not in contact with water at R.H. below 10%) of the thus obtained films were the following:

|  | Example 26 | Example 27 |
|---|---|---|
| break stress MPa | 29.4 | 33.2 |
| break strain % | 765 | 864 |
| tear strength N/m$^2$ at priming | 43(y) 76(x) | 47(y) 90(x) |
| tear strength N/m$^2$ at propagation | 43(y) 76(x) | 47(y) 90(x) |
| break energy Kj/m$^2$ | 6764 | 8441 |
| E (Young modulus) MPa | 425 | 365 |
| permeability to vapour (g · 30 μm/m$^2$ · 24 h) | 170 | 252 |
| permeability to liquid water | 90 | 101 |

|  | Example 26 | Example 27 |
|---|---|---|
| (g · 30 μm/m$^2$ · 24 h) | | |

(x) transversal
(y) longitudinal

Biodegradability tests carried out on the products obtained from the above example showed a substantial improvement in respect of the known conpositions. Particularly compositions comprising starch, poly-ethylene-vinyl alcohol and poly-epsilon-caprolactone under composting conditions have achieved a biodegradability up to 80% after only 10 days.

Shaped articles such as films, sheets, laminated films and sheets, filaments, fibers and injection molded articles produced from the herein described compositions by injection molding, extrusion, blow molding, extrusion blowing, thermoforming and similar conventional methods for the processing of thermoplastic martials fall within the scope of the invention.

Specific applications comprise films for absorbent articles, such as diapers and the like, for mulch and packaging in general, films for protective coatings or films coextruded with biodegradable and non-biodegradable polymers.

Absorbent articles are described in U.S. patent application Ser. No. 07/744,300, filed Aug. 13, 1991, the contents of which are hereby incorporated herein by reference.

Laminated films are described in U.S. patent application Ser. No. 07/741,131, filed Aug. 7, 1991, the contents of which are hereby incorporated herein by reference.

Compositions according to the invention comprising type A and type B polymers are useful to produce selective membranes for pervaporation processes as described in copending U.S. patent application entitled "Selectively-permeable membranes and the use thereof" (priority IT TO91A000327 of May 3, 1991) incorporated herein by reference.

TABLE 1

| Example | permeability* to H$_2$O vapour gr 30 μ/m$^2$ 24 h | break stress MPa | break strain (%) | E Module (MPa) | break energy (Kj/m$^2$) | tear strength long. (N/mm) | tear strength tras. (N/mm) |
|---|---|---|---|---|---|---|---|
| 1 | — | 38 | 830 | 290 | 8480 | — | — |
| 2 | 485 | 38 | 925 | 272 | 9370 | 107 | 109 |
| 3 | — | 25 | 1020 | 262 | 8450 | — | — |
| 4 | 408 | 27 | 840 | 310 | 7560 | — | — |

ASTM E 398-83;
T = 38° C.
U.R. 90%

TABLE 2

| Example | break stress (MPa) | break strain (%) | E Module MPa | break energy (Kj/m$^2$) | tear strength at priming (N/mm) | tear strength at propagation (N/mm) | permeability H$_2$O vap. (gr 30 μ/m$^2$ 24 h) | permeability H$_2$O liq. |
|---|---|---|---|---|---|---|---|---|
| 5 | 27.6 | 1080 | 339 | 10120 | 59.7(Y) 73 (X) | 59.7(Y) 73 (X) | 234 | 101 |
| 6 | 27.2 | 680 | 341 | 6012 | 41.3(X) 67 (Y) | 41.3(X) 67 (Y) | 212 | 104 |
| 7 | 31.5 | 651 | 414 | 6090 | 40.4(Y) 77 (X) | 40.4(Y) 77 (X) | 189 | 98 |
| 8 | 34.9 | 701 | 433 | 7260 | 49.5(Y) 91 (X) | 49.5(Y) 91 (X) | 270 | 90 |

X = transversal
Y = longitudinal

TABLE 3

| Example | 17 | 18* | 19* | 20* | 21* | 22 | 23 |
|---|---|---|---|---|---|---|---|
| Starch | 44.6 | 41.2 | 41.2 | 41.2 | 41.2 | 33 | 49 |
| EVOH | — | 32.9 | 24.66 | 32.9 | 24.66 | 32.9 | 20 |
| EAA | — | 3.1 | 3.1 | 3.1 | 3.1 | 2.5 | — |
| Armide E | — | 0.3 | 0.3 | 0.3 | 0.3 | 0.2 | 0.3 |
| Glycerine | 11.8 | 11.8 | 11.8 | 11.8 | 11.8 | 9.4 | 11.8 |
| H$_2$O | 2.5 | 2.5 | 2.5 | 2.5 | 2.5 | 2 | 2.5 |
| PCL based polymer | 41.1(a) | 8.2(b) | 16.44(b) | 8.2(c) | 16.44(c) | 20(b) | 16.4(b) |
| Torque (%) | 56 | 63 | 63 + 68 | 64 + 68 | 70 | 74 + 76 | 82–85 |
| Pressure (bar) | 21–31 | 18 | 18 + 23 | 17 + 18 | 21 | 17 + 20 | 25–27 |
| Final H$_2$O (% wt) | 3.8 | 3.97 | 3.46 | 3.23 | 3.26 | 2.12 | 3.7 |
| MFR (g/10') | 1.59 | 1.1 | 0.6 | 1.25 | 0.4 | 0.34 | — |
| $\sigma_b$ (MPA) | 9 | 20 | 15.6 | 19.7 | 16 | 23.2 | 17 |
| $\epsilon_b$ (%) | 529 | 277 | 221 | 312.4 | 302 | 422 | 131 |
| E (MPa) | 344 | 996 | 646 | 888 | 579 | 949 | 1158 |
| Er (Kj/m$^2$) | 2382 | 2385 | 1485 | 2595 | 2003 | 4062 | 1048 |

Starch: GLOBE 03401 (Cerestar), as such, instrinsic water content 12% wt
EVOH: poly-ethylene-vinyl alcohol, 44% ethylene molar content, hydrolysis degree 99.5
EAA: poly-ethylene - acrylic acid, Pow 5981, 20% wt acrylic acid
$\sigma_b$: break stress
$\epsilon_b$: break strain
(a:) poly-epsilon-caprolactone P-787 (Union Carbide)
(b): ε-caprolactone/diisocyanate copolymer Estane PCL 54353 BF Goodrich
(c): ε-caprolactone/diisocyanate copolymer Estane PCL 54351 BF Goodrich
Es.18*: preblending 80% EVOH + 20% PCL 54353
Es.19*: preblending 60% EVOH + 40% PCL 54353
Es.20*: preblending 80% EVOH + 20% PCL 54351
Es.21*: preblending 60% EVOH + 40% PCL 54351
MFR: melt flow rate (g/10 min) at 170° C., 5 kg load

We claim:

1. A polymeric composition obtainable from a melt comprising a starch component, a plasticizer and a synthetic thermoplastic polymer component, wherein the synthetic component comprises at least one polymer or mixture of polymers selected from the group consisting of:

(a) homopolymers of aliphatic hydroxyacids having from 2 to 24 carbon atoms, the corresponding lactones or lactides;

(b) copolymers of a first monomer selected from the group consisting of aliphatic hydroxyacids having from 2 to 24 carbon atoms, the corresponding lactones or lactides with a second monomer selected from the group consisting of aliphatic hydroxyacids having from 2 to 24 carbon atoms other than that constituting the first monomer, corresponding lactones or lactides, aromatic hydroxyacids, aliphatic or aromatic isocyanates;

(c) block or graft copolymers between the homopolymers and copolymers (a) or (b) with one or more of the following components:

(i) cellulose or modified cellulose;

(ii) amylose, amylopectin, natural or modified starches;

(iii) polymers deriving from reaction of diols, polyester prepolymers or polymers having diol terminal groups with:
   aromatic or aliphatic bifunctional isocyanates,
   aromatic or aliphatic bifunctional epoxides,
   aliphatic bicarboxylic acids,
   bicarboxylic cycloaliphatic acids,
   aromatic acids or anhydrides, (iv) polyurethanes, polyamide-urethanes from diisocyanates and aminoalcohols, polyamides, polyesteramides from bicarboxylic acids and aminoalcohols, polyester-urea from aminoacids and diesters of glycols, (v) polyhydroxylated polymers selected from the group consisting of polyvinylalcohol, ethylenevinylalcohol copolymers, totally or partially hydrolyzed, and polysaccharides up to dextrins, (vi) polyvinylpyrrolidone, polyvinylpyrrolidonevinylacetate copolymers, polyethyloxazolines;

(vii) ionomeric polymers selected from polyacrylates and polymetacrylates;

(d) polyesters obtained from monomers or comonomers as defined above at (a) and (b) upgraded with chain extenders selected from the group consisting of isocyanates, epoxides, phenylesters and aliphatic carbonates;

(e) polyesters obtained from monomers and comonomers defined at (a) and (b) above partially cross-linked by means of polyfunctional acids selected from the group consisting of trimellitic acid, pyromellitic acid, polyisocyanates and polyepoxides, said starch component and said synthetic polymer component being present in a ratio of from 1:9 to 9:1.

2. A composition according to claim 1, wherein the starch component and the synthetic polymeric component are in a weight ratio of from 1:4 to 4:1.

3. A composition according to claim 1, wherein the synthetic component comprises a polymer of an epsilon-hydroxyacid or a corresponding lactone selected from the group consisting of 6-hydroxycaproic, 6-hydroxyoctanoic and 3,7-dimetyl-6-hydroxyoctanoic acid.

4. A composition according to claim 3, wherein the synthetic component is a copolymer of an epsilon-hydroxyacid and an isocyanate selected from the group consisting of 4,4'-diphenylmethane-diisocyanate, toluilenediisocyanate, isophorondiisocyanate and hexanmetylenediisocyanate.

5. A composition according to claim 1, wherein the synthetic component comprises poly-epsilon-caprolactone or a copolymer of epsilon-caprolactone and an aliphatic or aromatic isocyanate or a mixture thereof.

6. A composition according to claim 5, wherein the synthetic component comprises poly-epsilon-caprolactone having a molecular weight above 40,000.

7. A composition according to claim 6, wherein the synthetic component comprises a mixture of poly-epsilon-caprolactone and copolymer of epsilon-caprolactone with an aliphatic or aromatic isocyanate in a weight ratio of from 5:1 to 1:1.

8. A composition according to claim 1, wherein the polymeric synthetic component comprises a component A selected from polymers (a) to (e) and mixtures thereof and a component B comprising a polymer derived from ethylenically unsaturated monomers, said polymer having repeating units provided with at least one functional polar group selected from the group consisting of hydroxyl, carboxyl, carboxyalkyl, alkylcarboxyl, pyrrolidyl, and acetal.

9. A composition according to claim 8, wherein component B comprises a polymer selected from the group consisting of polyvinylalcohol, ethylene-acrylic acid, ethylene-vinylacetate, ethylene-vinylalcohol, modified ethylene-vinylalcohol, modified polyvinylalcohol and mixtures thereof.

10. A composition according to claim 9, wherein component B comprises poly-ethylene-vinylalcohol obtained by hydrolysis of the corresponding poly-ethylene-vinylacetate, having an ethylene content lower than 44% by weight and hydrolysis degree of the acetate groups of from 50 to 100%.

11. A composition according to claim 8, wherein components A and B are present in a weight ratio of from 1:6 and 6:1.

12. A composition according to claim 8, comprising:
from about 20 to about 60% by wt of the starch component,
from about 10 to about 80% by wt of component A, and
from 0 to about 45% by wt of component B, the percent amounts being expressed with reference to the sum of the starch and total synthetic component.

13. A composition according to claim 12, comprising from about 10 to about 50% by wt of component A and from about 2 to about 30% by wt of component B.

14. A composition according to claim 8, comprising:
from about 5 to about 60% by wt of the starch component,
from about 40 to about 80% by wt of component A, and
from 0 to about 35% by wt of component B, the percent amounts being expressed with reference to the sum of the starch and total synthetic component.

15. A composition according to claim 14, comprising from about 5 to about 30% by wt of component B.

16. A composition according to claim 1 or 8, comprising from 1 to 50% by weight, based on the weight of the starch/synthetic polymer system, of a plasticizer selected from the group consisting of glycerine, polyglycerol, glycerol ethoxylate, ethylene or propylene glycol, ethylene or propylene diglycol, ethylene or propylene triglycol, polyethylene or polypropylene glycol, 1,2-propandiol, 1,3-propandiol, 1,2-, 1,3-, 1,4-butandiol, 1,5-pentandiol, 1,6-, 1,5-hexandiol, 1,2,6-, 1,3,5-hexantriol, neopentylglycol, trimethylolpropane, pentaerythritol, sorbitol, sorbitol acetate, sorbitol diacetate, sorbitol monoethoxylate, sorbitol dipropoxylate, sorbitol diethoxylate, sorbitol hexaethoxylate, aminosorbitol, trihydroxymethylaminomethane, glucose/PEG, the product of reaction of ethylene oxide with glucose, trimethylolpropane monoethoxylate, mannitol monoacetate, mannitol monoethoxylate, butyl glucoside, glucose monoethoxylate, alphamethyl glucoside, the sodium salt of carboxymethylsorbitol, polyglycerol monoethoxylate and mixtures thereof.

17. A composition according to claim 16, wherein the plasticizer is present in the amount of from 5 to 25% by weight with reference to the weight of the total composition consisting of the starch and polymeric component (s).

18. A composition according to claim 16, wherein the plasticizer is selected from glycerine, sorbitol and sorbitol monoethoxylate and mixtures thereof.

19. A composition according to claim 16, comprising urea in the amount of from 0.5 to 20% by wt with reference to the weight of the total composition.

20. A composition according to claim 1 or 8, comprising up to 5% by wt with reference to the overall composition of a hydrophobic polymer selected from the group consisting of polyethylene, polypropylene and polystyrene.

21. A composition according to claim 1 or 8, having a water content of from 1.5 to 5% by wt with reference to the overall composition.

22. A composition according to claim 1 or 8, wherein the starch component comprises more than 78% by wt of amylopectin.

23. A composition according to claim 1 or 8, comprising of from 0.01 to 10% by wt, with reference to the weight of the starch component, of an additive selected from the group consisting of boric acid, borax, metaboric acid, aluminium hydroxide and alkali-metal salts.

24. A composition according to claim 23, wherein the starch component has an amylopectin content higher than 70% by wt.

25. A thermoplastic polymeric composition including starch component, a synthetic thermoplastic polymer component and a plasticizer, wherein the synthetic thermoplastic component comprises blends of both (1) a polymer selected from the group consisting of ethylene-vinylalcohol copolymer and polyvinylalcohol and (2) an aliphatic polyester, and the plasticizer is selected from the group consisting of:
(a) polyols formed by from 1 to 20 repeating hydroxylated units each including from 2 to 6 carbon atoms,
(b) ethers, thioethers, inorganic and organic esters, acetals and amino-derivatives of polyols formed by from 1 to 20 repeating hydroxylated units, each including from 2 to 6 carbon atoms,
(c) reaction products of polyols having from 1 to 20 repeating hydroxylated units, each including from 2 to 6 carbon atoms, with chain extenders,
(d) oxidation products of polyols having from 1 to 20 repeating hydroxylated units, each including from 2 to 6 carbon atoms, including at least one aldehydic or carboxylic functional group or a mixture thereof, said starch component and said synthetic polymer component being present in a ratio of from 1:9 to 9:1.

26. Articles, including films, sheets, fibres and filaments when obtained by the use of a polymeric composition according to any one of claims 1 or 8.

27. A composition according to claim 11, wherein components A and B are present in a weight ratio of from 1:4 to 4:1.

* * * * *